(12) United States Patent
Dunne et al.

(10) Patent No.: US 7,909,264 B2
(45) Date of Patent: Mar. 22, 2011

(54) DISCHARGE DEVICE AND METHOD FOR EVAPORATING A LIQUID AND EVAPORATOR

(75) Inventors: Stephen Terence Dunne, Stowmarket (GB); Marc Rohrschneider, Hagen (DE); Gert Blankenstein, Dortmund (DE)

(73) Assignee: Boehringer Ingelheim microParts GmbH, Dortmund (DE)

( * ) Notice: Subject to any disclaimer, the term of this patent is extended or adjusted under 35 U.S.C. 154(b) by 377 days.

(21) Appl. No.: 11/577,647

(22) PCT Filed: Jul. 19, 2005

(86) PCT No.: PCT/EP2005/007851
§ 371 (c)(1),
(2), (4) Date: Apr. 20, 2007

(87) PCT Pub. No.: WO2006/045359
PCT Pub. Date: May 4, 2006

(65) Prior Publication Data
US 2008/0087737 A1   Apr. 17, 2008

(30) Foreign Application Priority Data
Oct. 20, 2004   (GB) .................................. 0423243.5

(51) Int. Cl.
*A24F 25/00* (2006.01)
*A61L 9/04* (2006.01)
*B05B 7/32* (2006.01)
*B05B 1/14* (2006.01)
*F23D 14/68* (2006.01)

(52) U.S. Cl. ................ 239/44; 239/34; 239/49; 239/57; 239/58; 239/337; 239/590

(58) Field of Classification Search .................... 239/34, 239/43, 44, 47, 49, 57, 58, 59, 309, 337, 239/340, 354, 373, 590
See application file for complete search history.

(56) References Cited

U.S. PATENT DOCUMENTS

| | | | | |
|---|---|---|---|---|
| 3,587,968 A * | 6/1971 | Hennart et al. | ................ | 239/47 |
| 4,200,229 A * | 4/1980 | Spector | ........................ | 239/57 |
| 4,346,059 A * | 8/1982 | Spector | ........................ | 422/125 |
| 5,810,253 A * | 9/1998 | Ohayon | ........................ | 239/43 |
| 6,109,539 A * | 8/2000 | Joshi et al. | ..................... | 239/43 |
| 6,595,441 B2 * | 7/2003 | Petrie et al. | ................... | 239/345 |
| 6,923,383 B1 * | 8/2005 | Joshi et al. | ..................... | 239/302 |
| 2002/0158156 A1 | 10/2002 | Joshi et al. | | |
| 2002/0168301 A1 | 11/2002 | Channer | | |
| 2003/0047618 A1 | 3/2003 | Dobyns et al. | | |
| 2003/0132305 A1 | 7/2003 | Joshi et al. | | |

FOREIGN PATENT DOCUMENTS
EP        1 442 754        8/2004
* cited by examiner

*Primary Examiner* — Dinh Q Nguyen
*Assistant Examiner* — Ryan Reis
(74) *Attorney, Agent, or Firm* — Roberts Mlotkowski Safran & Cole, P.C.; David S. Safran

(57) ABSTRACT

A discharge device and a method for evaporating a liquid to the atmosphere are proposed. The liquid pressurized by gas is supplied to an evaporator via a flow restriction device which restricts the flow rate of the liquid such that continuous release and evaporation of the liquid is possible. Further, an evaporator is proposed. The evaporator comprises an evaporation surface which is designed preferably by microstructuring such that the surface area is increased and/or the liquid forms an essentially uniform film on the evaporation surface.

38 Claims, 8 Drawing Sheets

DISCHARGE DEVICE AND METHOD FOR EVAPORATING A LIQUID AND EVAPORATOR

BACKGROUND OF THE INVENTION

1. Field of the Invention

The present invention relates to a discharge device for evaporating a liquid using a container with pressurized liquid and a release valve. The invention also relates to an evaporator for evaporating a liquid and to a method for evaporating a liquid to the atmosphere. In particular, the present invention relates to the dispensing of any active ingredient such as fragrances, perfumes, air fresheners, pharmaceuticals or the like, preferably in enclosed spaces.

2. Description of Related Art

Many continuous liquid delivery devices are on the market or have been proposed. There are two main types, namely passive and active devices. In passive devices, a liquid is absorbed, diluted or dissolved in a carrier such as a gel, foam or liquid solvent. In such passive devices, the transfer of the liquid or any active ingredient to the atmosphere depends on the rate of evaporation, which is dependent on room temperature and the rate of air circulation.

Many different continuous and non-continuous active devices have been proposed or are commercially available. Some are based on passive devices with the addition of an evaporation enhancer such as an electrical heater or air fan. Others are only intermittently continuous and rely on a user pressing a button to release an aerosolized cloud of liquid containing the active ingredient that then evaporates in the atmosphere. Typical devices of this kind are wall-mounted pressurized aerosol cans, which are activated directly by a user when the user presses a lever or any other actuator, or indirectly by a user when, for instance, a door is opened.

SUMMARY OF THE INVENTION

An aspect of the present invention is to provide a discharge device and a method for evaporating a liquid as well as an evaporator, wherein a more uniform and/or continuous release and evaporation of liquid is possible. In particular, any dependency on room temperature and air circulation can be avoided or at least reduced, and any periodic, direct or indirect activation by a user or by any electrical device is not necessary.

A basic idea of the present invention is to use a flow restriction device for restricting the flow rate of the pressurized liquid from a container to the evaporator so that no intermittent operation of a valve or the like is required. Instead, a valve for activating and deactivating the device can be opened permanently—this means at least for a long time period and/or without the necessity of frequently closing—for continuous release and evaporation of the liquid. This allows very simple handling. Further, the flow restriction device determines the flow rate and, thus, the actual rate of evaporation. Therefore, the dependency of the evaporation rate on room temperature, air circulation or the like can be avoided or at least reduced.

Preferably, the flow restriction device comprises at least one channel, in particular a long capillary channel, which restricts the flow of liquid as desired.

The active source of energy is preferably gas which may be liquefied gas or a compressed gas. The gas is stored together with the liquid or any active ingredient, preferably plus a solvent or bulking agent, if needed, in a pressurized container.

In the present invention, the term "liquid" has to be understood in a broad sense. In particular, it shall cover all kinds of ingredients, liquids, fluids, mixtures, suspensions, liquefied gases, or the like that may be evaporated. Preferably, the liquid is or contains an oil, a solvent, a fragrance, a perfume, an air freshener, a pharmaceutical, a therapeutic or any other active ingredient or the like.

A further aspect of the present invention is directed to an evaporator for evaporating the liquid. The evaporator comprises an evaporation surface, which is designed preferably by micro-structuring such that the surface area is increased and/or the liquid forms an essential uniform film on the evaporation surface. Thus, the dependency of the evaporation rate on room temperature, air circulation or the like can be avoided or at least reduced.

Further aspects, advantages and features of the present invention will be apparent from the following detailed description of preferred embodiments.

DETAILED DESCRIPTION OF THE INVENTION

In the figures, the same reference signs are used for same or similar components, wherein same or similar characteristics or advantages are achieved even if a repeated discussion is omitted.

Figure 1:
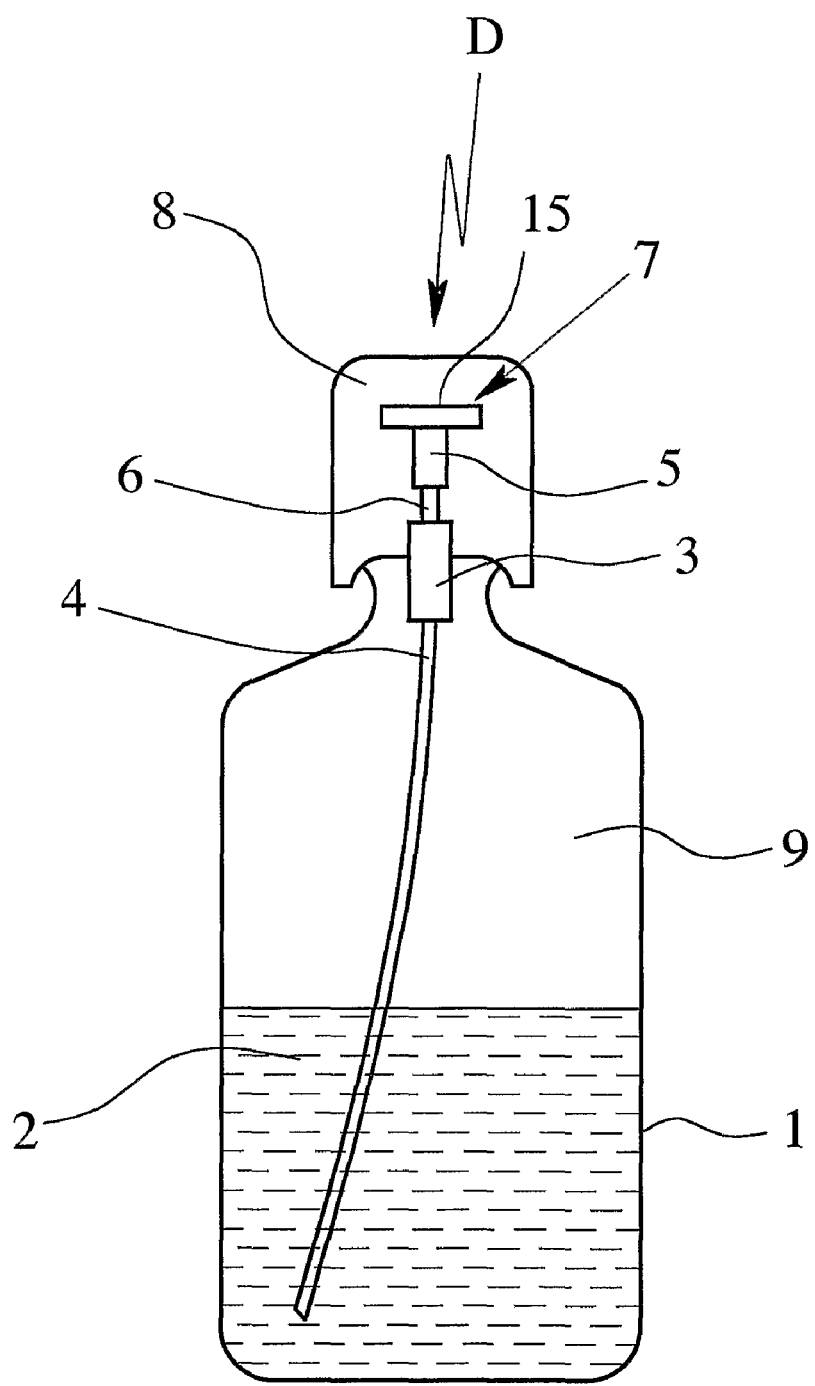
FIG. 1 is a schematic section of a discharge device with a flow restriction device and an evaporator according to a first embodiment.

FIG. 1 shows a schematic section of a discharge device D according to a first embodiment of the present invention. The discharge device D comprises a container 1 with a liquid 2. The liquid 2 comprises preferably an active ingredient, a solvent and/or a liquid and compressed gas. Reference is made to the above understanding of the term "liquid."

The liquid 2 may be placed in a bag (not shown) in the container 1 with the gas outside the bag. Either a conventional bag or a bag on valve system may be used. Also, a piston in the container 1 may be used to separate the gas and liquid 2 if desired or required. If a piston is used the gas may be replaced by a biasing means such as a spring. However, these can be provided also by other means for pressurizing the fluid 2 in the container 1.

The discharge device D comprises, optionally, a valve 3 that is preferably mounted at the top of the container 1 and comprises preferably a dip tube 4 reaching down to the bottom of the container 1.

The valve 3 is preferably a conventional aerosol valve or the like. This simplifies assembly and filling. The valve 3 is preferably of the on/off-type. However, the valve 3 can also be designed such that it can be only opened once. In this case, the valve 3 can be formed by a removable lid, cap or the like. Alternatively, a metered dose valve could be used. In this way every time the valve is opened a precise metered amount of liquid 2 is released. Preferably, the valve 3 can be locked in its open and/or closed state.

The discharge device D further comprises a flow restriction device 5 which is preferably connected fluidically with the container 1/valve 3 via a stem 6. Thus, the flow restriction device 5 is placed after the valve 3. However, it is also possible to place the flow restriction device 5 before the valve 3 and/or to integrate the flow restriction devices into the valve 3. Alternatively, the dip tube 4 can also be replaced by the flow restriction device 5 or form the flow restriction device 5.

The discharge device D further comprises an evaporator 7 which is fluidically connected to the outlet of the flow restriction device 5 for supplying the liquid 2 for evaporation.

The discharge device D comprises optionally an actuator 8. The actuator 8 may be mounted on the container 1 and/or the valve 3 such that the valve 3 can be opened by pressing down the actuator 8. Preferably, the actuator 8 is designed in such a way that once valve 3 is opened it stays open after the user ceases to press the actuator 8. This can be achieved by a ratchet mechanism, a locking mechanism or the like.

Preferably, the actuator 8 has a locking mechanism that allows the user to turn valve 3 on and leave it in the open position. The locking mechanism may lock the valve 3 in the open position permanently or may have an on/off-feature.

A metered dosed valve or any other metering device may be incorporated to limit the amount of liquid 2 released after each actuation or every time the actuator 8 is locked in the open position.

The container 1 can be used with the valve 3 on top, in which case the conventional dip tube 4 is used. Alternatively, the container 1 may be used in the inverted position with the actuator 8 at the base, in which case the dip tube 4 is not needed.

It has to be noted that the flow restriction device 5 can also be located in or integrated into the actuator 8.

Preferably, liquid 2 is pressurized in the container 1 by gas, in particular liquefied or compressed gas. If liquid gas is used it may be any hydrocarbon such as butane, propane or DME or any suitable HFA gas, such as 134a. Any percentage of liquefied gas by mass may be used depending on the application. For containers with a life expectancy of 1 to 3 months the preferred percentage of gas by mass is preferably between 5 and 50%. If the liquefied gas is dissolved in the liquid 2, in particular in the active ingredient/solvent mixture, the pressure in the container 1 may be less than the vapor pressure of the pure gas.

If a compressed gas is used, a pressure regulating element (not shown) may be incorporated to keep the flow of liquid 2 constant, independent from pressure changes which will take place as liquid level drops in the container 1 and the space 9 above the liquid 2 is filled by the gas increase. The pressure regulating element may regulate the pressure into the flow restriction device 5 automatically or may be controlled by the user, for instance, by twisting the actuator 8 to decrease the flow restriction as the pressure in the container drops with use. The pressure regulating device may be incorporated into the flow restriction device 5 as explained later. Any compressed gas may be used such as air, nitrogen or $CO_2$.

The pressure in the container 1 is preferably between 5 hPa and 1 MPa, preferably between 50 hPa and 0.2 MPa. This applies in particular at atmospheric or room temperature.

The flow restriction device 5 restricts the flow rate of liquid 2 from the container 1 to the evaporator 7 in the open state of the valve 3 below or substantially equal to the possible rate of evaporation of the liquid 2 by the evaporator 7. Thus, the valve 3 can be opened permanently for continuous release from the container 1 and evaporation of the liquid 2 by the evaporator 7.

The flow restriction device 5 preferably restricts the flow rate of liquid 2 such that the flow rate is 0.01 to 2.0 g/d (grams per day), most preferably 0.05 to 0.5 g/d. This is a relatively low, reasonable range suitable for most applications, in particular for air fresheners or the like.

The useable lifetime of the discharge device D is preferably between 2 and 36 weeks, i.e., with permanently opened valve 3. With closed valve 3, the discharge device D can be stored for at least more than one year.

Figure 2:
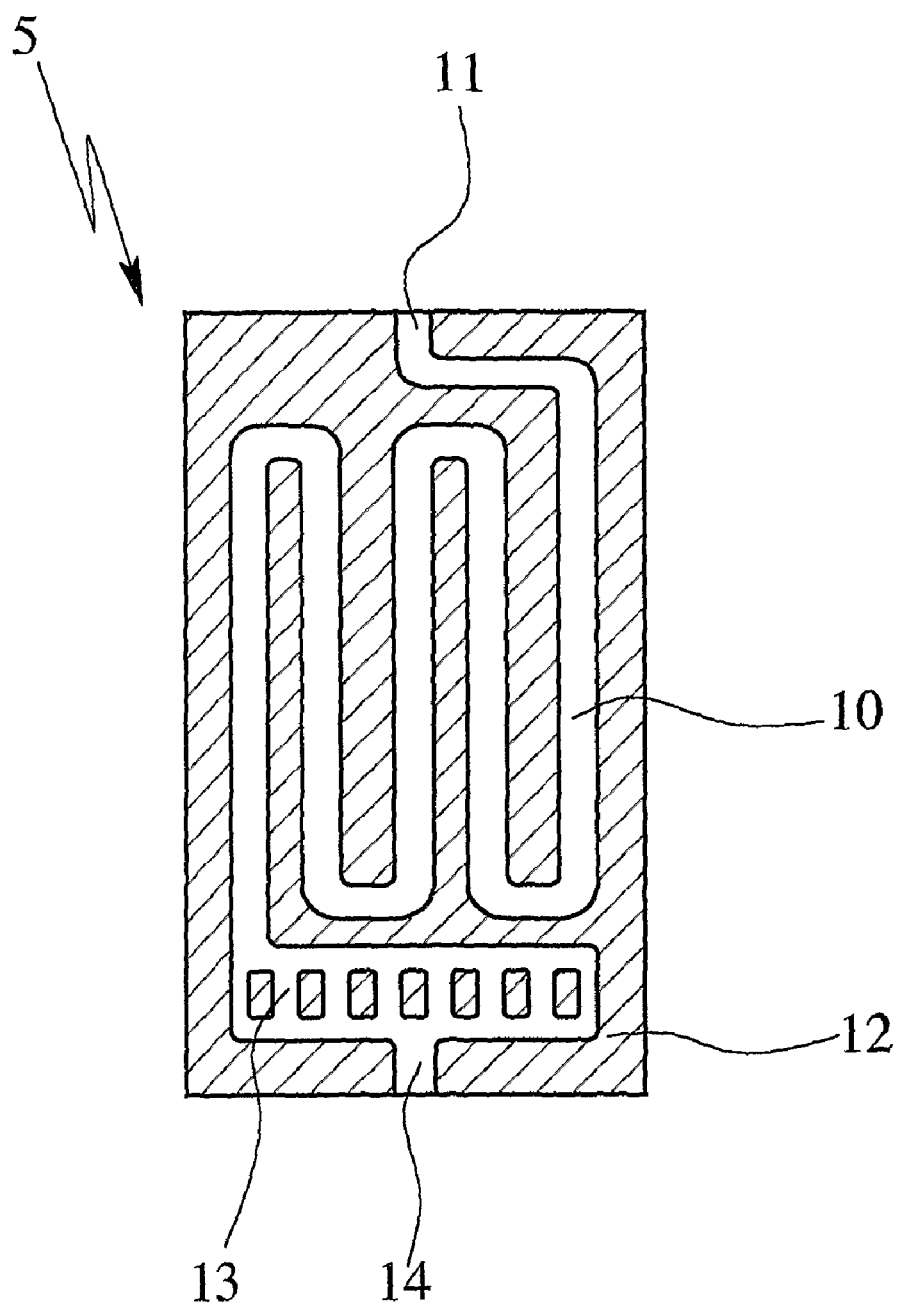
FIG. 2 is a schematic section of the flow restriction device of the first embodiment.

According to the most preferred embodiment, the flow restriction device 5 comprises at least one throttle channel 10, preferably a long capillary tube or channel 10, as shown in the schematic section of the flow restriction device 5 according to FIG. 2.

The required length and diameter of the channel 10 can be calculated by using the classical laminar flow equations once the flow rate, pressure and viscosity and density of the liquid 2 are known. The shorter the length of the channel 10, the smaller is the hydraulic diameter required for any given flow rate and set of physical parameters.

The diameter should be as large as possible to minimize clogging or blocking. Preferably, the average or hydraulic diameter of the channel 10 is between 1 μm and 1 mm, more preferably between 50 and 200 μm, in particular between 75 and 125 μm. The cross section of the channel 10 may have any suitable form and does not have to be necessarily circular.

The length is also a factor determining the flow resistance and, thus, the flow rate, Preferably, the length of the channel is between 1 mm and 10 m, more preferably between 10 mm and 1 m.

In the illustrated embodiment, the channel 10 has a meander shape. However, the channel 10 may also be essentially straight or take the shape of a spiral, as shown in another embodiment described later.

In a further embodiment, the channel 10 has or forms a portion with higher capillary forces, in particular due to a reduced diameter or cross section, in order to avoid that the channel 10 empties completely when the evaporation rate is much higher than the flow rate. This portion (not shown) is preferably formed near the outlet valve of the fuel restriction device 5 and/or of the channel 10.

According to a further embodiment (not shown), the flow restriction device 5 comprises multiple channels 10 connected in parallel. The use of the respective channels 10 is preferably variable (at least one of the channels 10 can be individually blocked) for changing the flow rate. In particular, this arrangement may form the pressure regulating device mentioned-above, wherein the channels 10 can be opened sequentially as the pressure drops in the container 1 to decrease flow restriction. Preferably, the user may switch from one flow rate to at least one other flow rate by pressing a button, turning the actuator 8, operating any other element or the like. Thus, the flow rate is adjustable. However, there are also other possibilities that can be used to adjust the flow rate, in particular by varying the effective length or diameter of the channel 10 and/or by additional measures, like a throttle valve (not shown) or the like.

Preferably, the flow restriction device 5 comprises a molded body 12, preferably made of plastic, as shown in FIG. 2, which forms the channel(s) 10 and optionally a filter 13 upstream of the channel 10. The structured body 12 and/or the channel 10 or any other flow restriction structure can be made of any suitable material and/or structured with any other suitable method other than molding.

The structured body 12 is preferably covered by a lid, film or any other suitable covering (e.g. covering 16 shown in FIG. 5), so that the liquid 2 supplied by the stem 6 can only enter into the flow restriction device 5/the filter 13 via the inlet 14 and leave the flow restriction device 5 via the outlet 11, wherein evaporation of the liquid 2 is prevented in the flow restriction device 5. Preferably, the molded body 12 is sealed by heat-sealing a film or the like on the surface of the body 12 or by ultrasonically welding a second plastic molding, cover or the like over the surface forming a passageway, i.e., at least the channel 10 and optionally the filter 13, with the molded body 12.

The filter 13 prevents blocking or clogging of the channel 10. Preferably, the filter 13 has filter bores or openings of smaller size than the diameter of the subsequent channel(s) 10 to filter out any problematic particles in the liquid 2.

In the first and preferred embodiment, the filter 13 is integrated into the flow restriction device 5 and/or the body 12. However, the filter 13 can also be made and/or arranged separately from the flow restriction device 5. For example, the filter 13 could be integrated into the stem 6 or the valve 3. In any case, the filter 13 is preferably arranged upstream in series with the flow restriction device 5 or at least its channel 10.

According to another embodiment (not shown), the flow restriction device 5 may comprise additionally or alternatively at least one restriction orifice, preferably with a hydraulic diameter of 30 to 100 μm, in order to reduce or restrict the flow rate of the liquid 2 as desired. The advantage of the restriction orifice arrangement over the channel arrangement is its overall smaller size. The disadvantage is its higher susceptibility to blockage.

The evaporator 7 is fluidically connected to the flow restriction device 5, in particular to its outlet 11. The construction of the evaporator 7 will be discussed in more detail with reference to the other figures and embodiments.

In the first embodiment, the flow restriction device 5 and the evaporator 7 are preferably arranged adjacent to each other, in particular one above the other. It is also possible to integrate the flow restriction device 5 into the evaporator 7 or vice versa. Alternatively or additionally, the evaporator 7 may be integrated into the actuator 8 of the discharge device D.

The evaporator 7 may comprise a plastic plate with molded grooves, a sponge like material, adsorbent paper or a conical cup or any other device that can hold liquid 2 while it evaporates. It is preferably placed within the actuator 8 and protected with a cap, cover, screen or the actuator 8 to prevent users coming into direct contact with the liquid 2. A total exposed area of the evaporator 7 is large enough to evaporate the liquid 2 at a rate at least substantially equal or larger than the flow rate of liquid 2 through the flow restriction device 5.

According to the present invention, the evaporator 7 for evaporating the liquid 2 comprises an evaporation surface 15 (as indicated in FIG. 1), which is designed such that the surface area is increased and/or the liquid 2 forms an essentially uniform film on the evaporation surface 15. Preferably, the evaporation surface 15 is micro-structured to achieve these properties.

In the following, further embodiments of the present invention are described with reference to the further figures, wherein only essential differences will be emphasized. Thus, the above explanation applies in addition as well.

Figure 3:
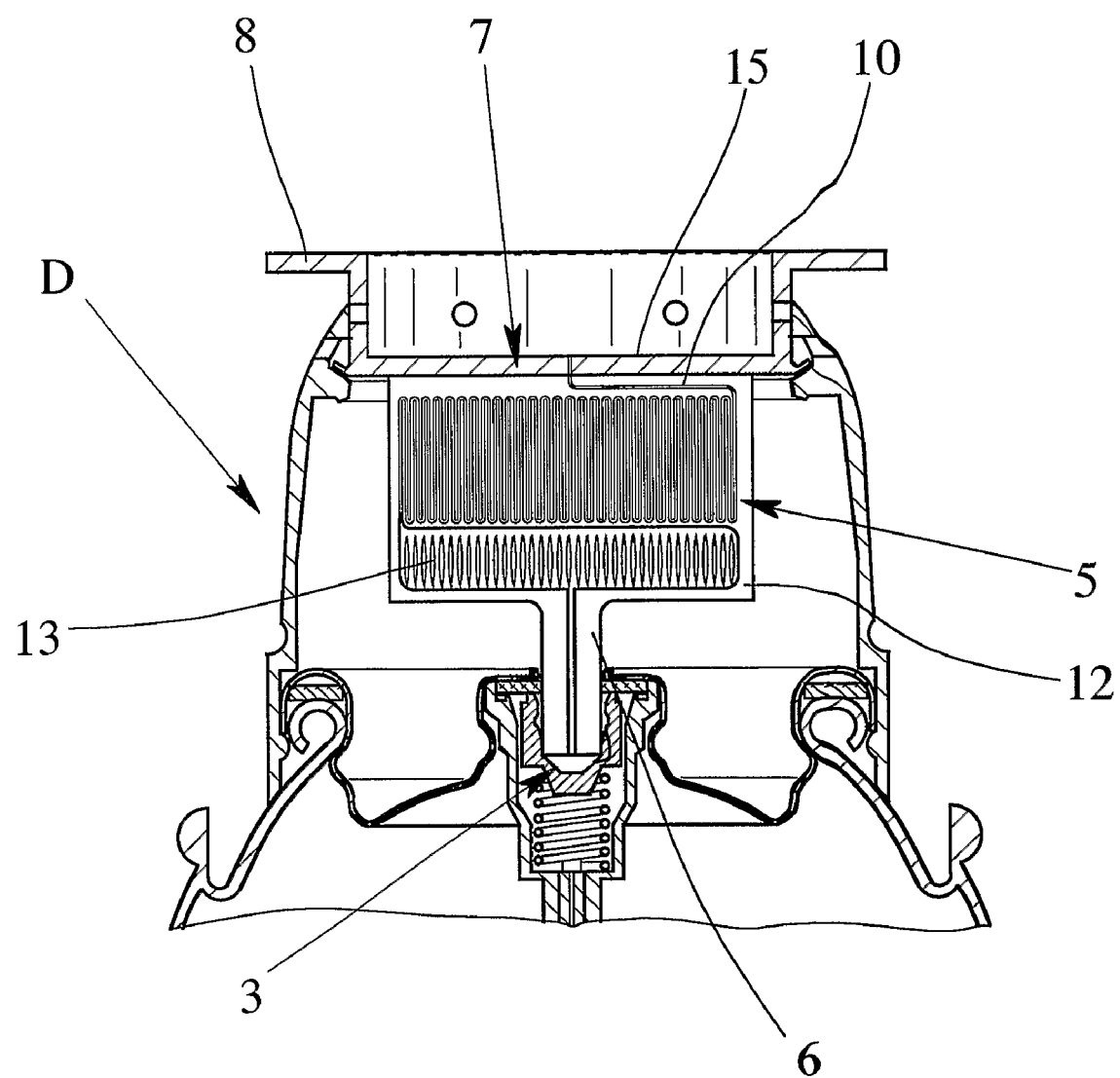
FIG. 3 is a schematic section of a part of a discharge device according to a second embodiment in the closed state.

FIG. 3 shows a second embodiment of the discharge device D with closed valve 3. The flow restriction device 5 is arranged substantially vertical and essentially perpendicular to the horizontal evaporation surface 15 of the evaporator 7 located above. The channel 10 takes the form of a meander as in the first embodiment and guides the fluid directly to the evaporator 7, in particular to its surface 15.

Valve 3 can be opened by depressing the actuator 8. If actuator 8 is depressed and locked in this position, the valve 3 is permanently open until the actuator 8 is unlocked, e.g., by twisting.

Preferably, the stem 6 is integral with the floor restriction device 5 or body 12 and includes a feed channel for supplying fluid 2 from the valve 3.

Figure 4:
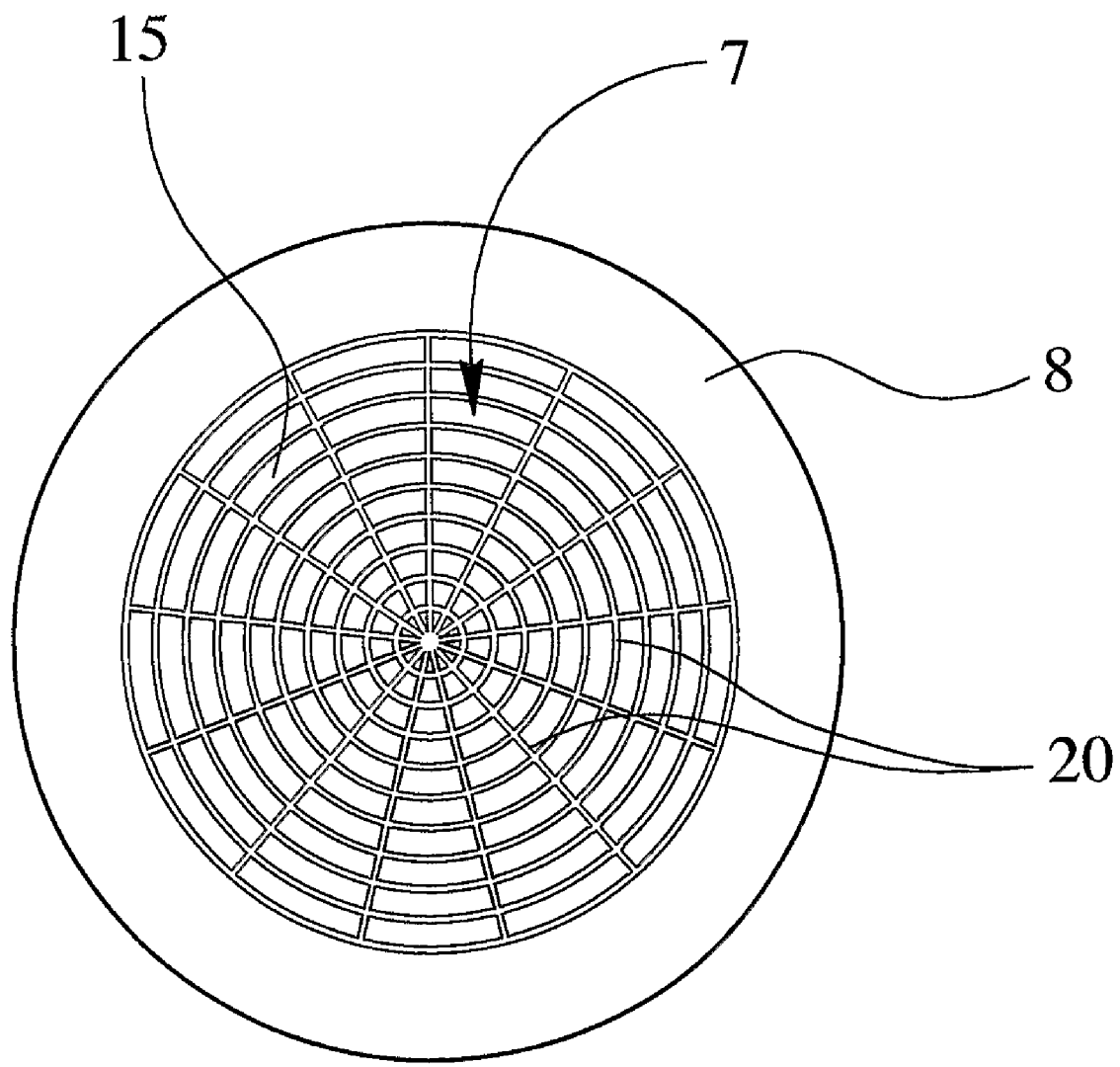
FIG. 4 is a schematic view of an evaporator of the discharge device according to the second embodiment.

FIG. 4 shows a spider-net-like structure of grooves 20 on the evaporation surface 15. These grooves 20 or similar structures promote the forming of a uniform film of liquid 2 on the evaporation surface 15. Further, a central supply channel for supply with fluid 2 from the flow restriction device 5 is shown.

Figure 5:
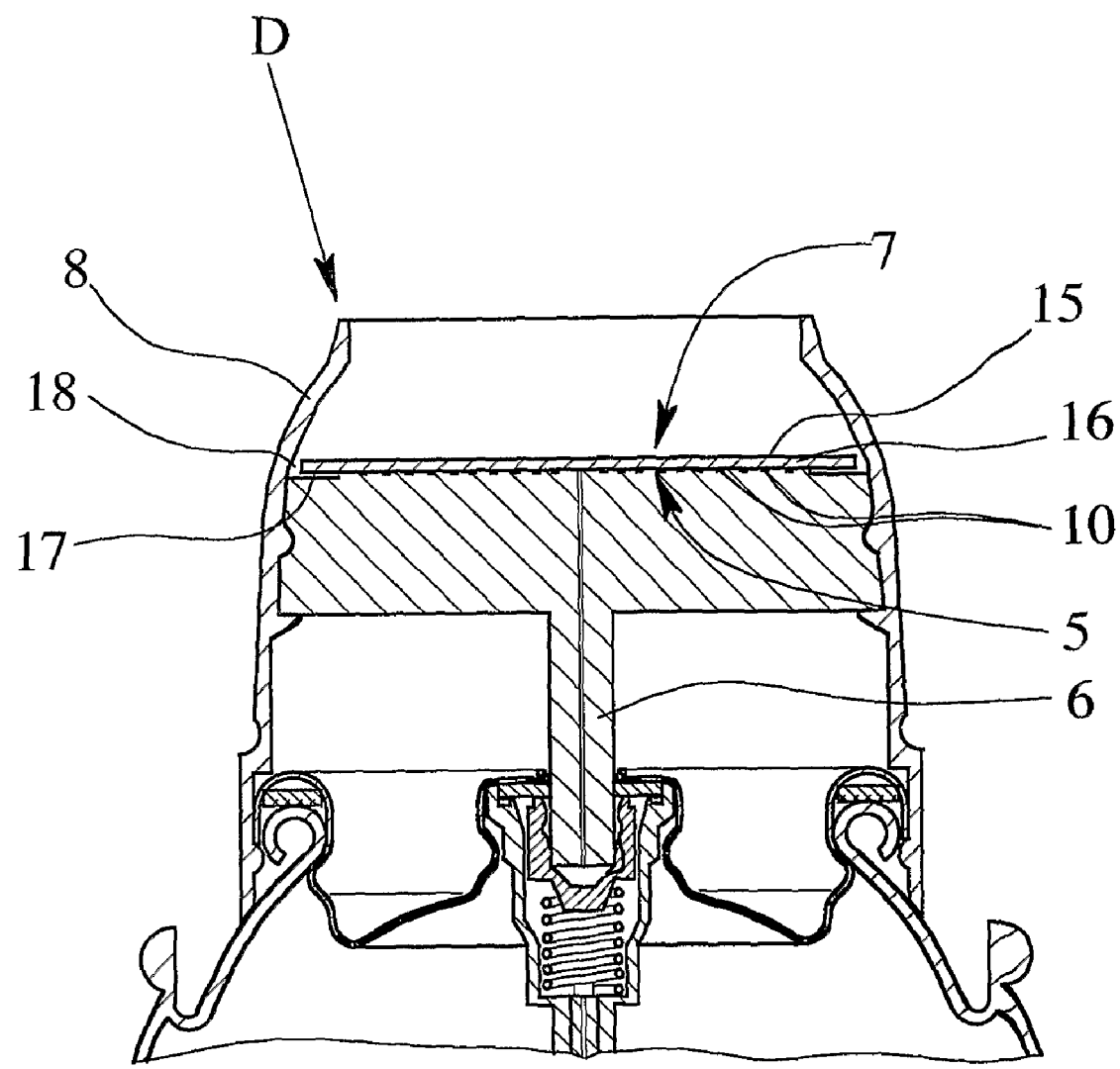
FIG. 5 is a schematic perspective section of a part of a discharge device with a flow restriction device according to a third embodiment.

FIG. 5 shows a third embodiment of the discharge device D with closed valve 3. The flow restriction device 5—in particular its channel 10 in spiral form—is arranged substantially horizontal and essentially parallel to the horizontal evaporation surface 15 of the evaporator 7 located above. In particular, the evaporator 7 forms the covering 16 or, vice versa, the covering 16 of the floor restriction device 5 forms the evaporation surface on its upper face.

Figure 6:
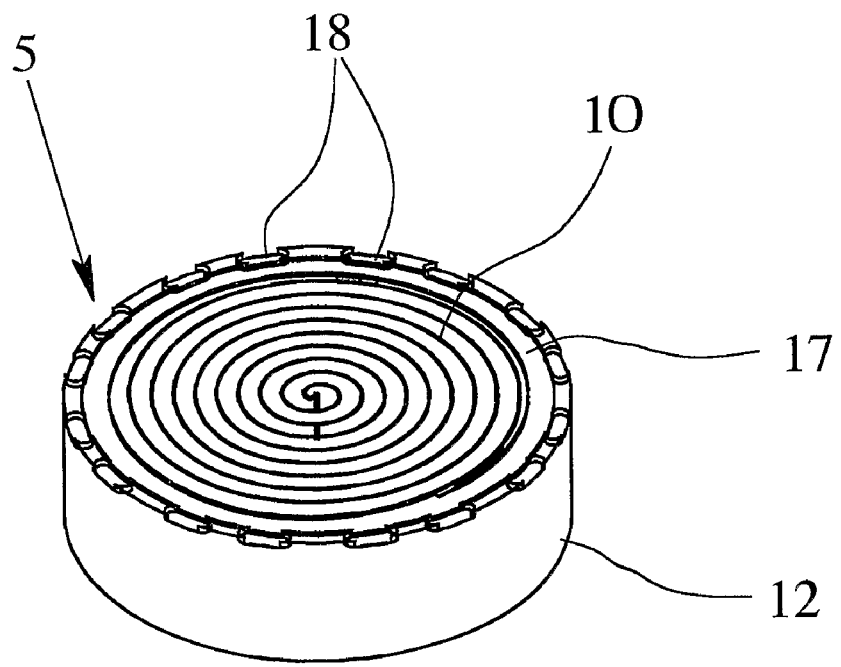
FIG. 6 is a perspective view of the flow restriction device according to the third embodiment.

FIG. 6 shows the enlarged flow restriction device 5 without the covering 16. The spiral form of the channel 10 is clearly visible. Further, a circumferential ring space 17 for liquid 2 is provided. This forms a liquid buffer. The radial depressions, notches or grooves 18 form either evaporation areas or a fluidic connection so that the liquid 2 can flow around the covering 16 and up to the evaporation surface 15.

Figure 7:
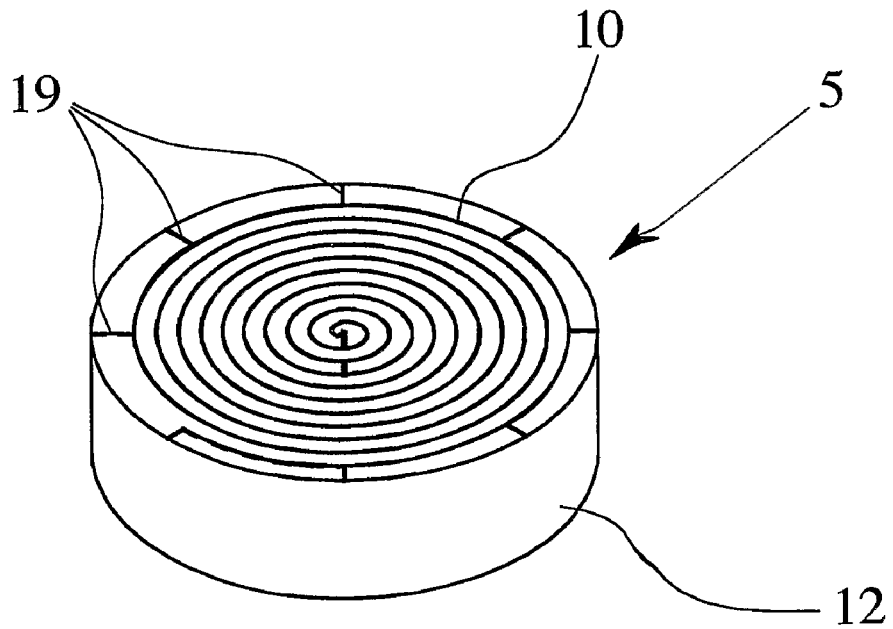
FIG. 7 is a perspective view of a flow restriction device according to a fourth embodiment.

FIG. 7 shows a fourth embodiment of the flow restriction device 5 without covering 16 and without the associated evaporator 7. The spiral form of the channel 10 is clearly visible. Further, radial channel connections 19 are provided. Depending on the rotational position of the actuator 8 or the like at least one of the channel connections 19 can be connected with the evaporator 7 (not shown). The effective length of the channel 10 varies depending on the respectively connected channel connections 19. Thus, the flow rate of liquid 2 can be adjusted.

According to an alternative (not shown), at least two channels 10 forming two parallel spirals can be provided and connected in parallel or in series, as desired. Individual blocking can be used to vary the effective length to adjust the flow resistance and, thus, the flow rate.

Figure 8:
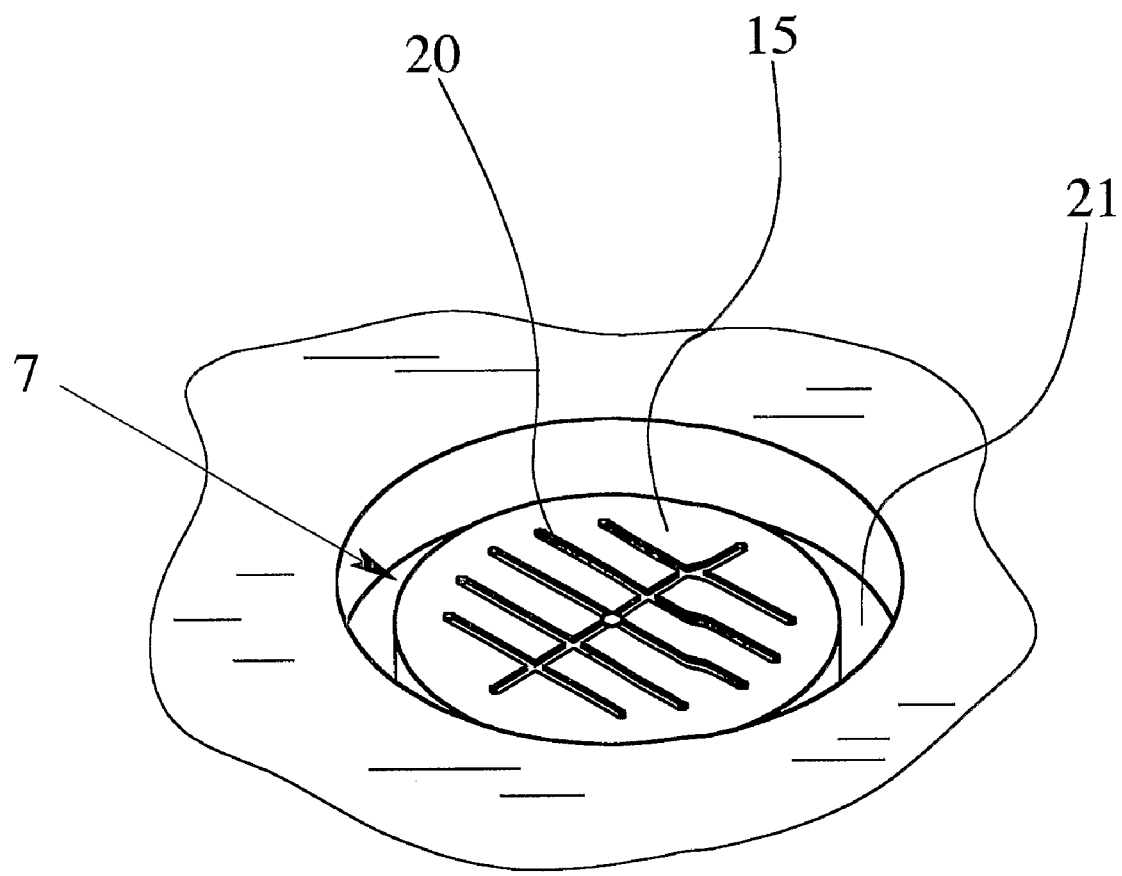
FIG. 8 is a partial perspective view of an evaporator according to a fifth embodiment.

FIG. 8 shows a fifth embodiment of the evaporator 7. The evaporation surface 15 comprises a grid of grooves or recesses 20. These grooves, recesses 20 or similar structures promote the forming of a uniform film of liquid 2 on the evaporation surface 15. In addition, the surface 15 is surrounded by a circumferential groove 20 that is deeper so that is does not fill with liquid 2. This ring groove 21 forms an outer limit for the liquid 2 on the surface 15.

Figure 9:
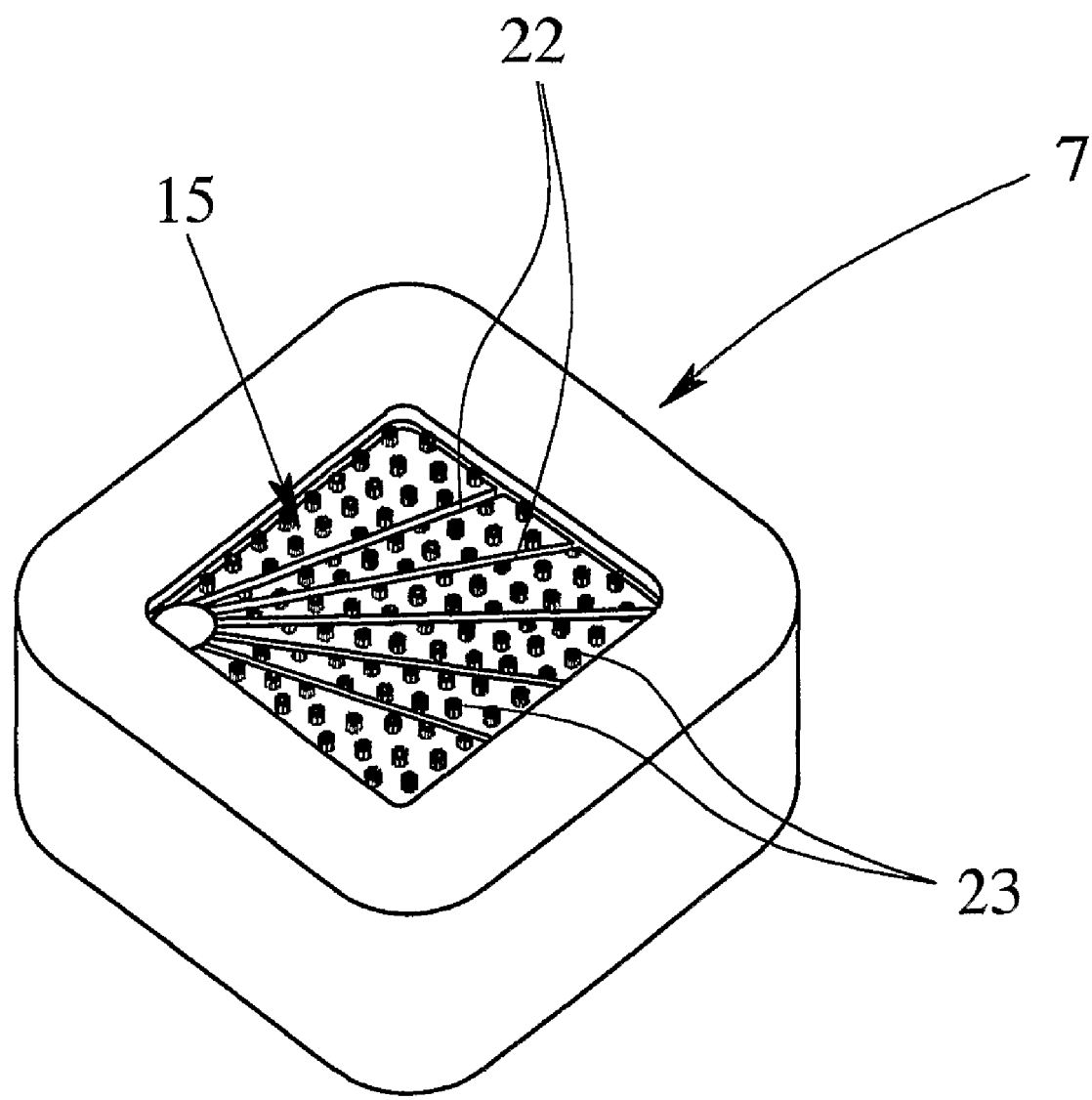
FIG. 9 is a perspective view of an evaporator according to a sixth embodiment.

FIG. 9 shows a sixth embodiment of the evaporator 7. The evaporation surface 15 comprises another grid of grooves 22 and microstructures, like posts 23 or the like. These structures 23 increase the total surface area that is covered by the liquid 2 and, thus, increase the rate of evaporation.

The respective features of the different embodiments can be combined as desired or interchanged.

What is claimed is:

1. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the channel is one of a spiral or a meander shape;
wherein the flow restriction device comprises at least one capillary channel.

2. Discharge device according to claim 1, in combination with a pressurized liquid held in the container.

3. Discharge device according to claim 2, wherein the liquid is or contains one of at least an oil, a solvent, a fragrance, a perfume, an air freshener, a pharmaceutical, a therapeutic and any other active ingredient.

4. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the liquid is pressurized by one of liquified gas or compressed gas;
wherein the at least one channel comprises at least one capillary channel.

5. Discharge device according to claim 2, wherein the pressure of the liquid is between 5 hPa and 1 MPa.

6. Discharge device according to claim 1, wherein the valve can be only opened once or is an on/off-type of valve.

7. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the valve can be locked in the open state;
further comprising an actuator for actuating the valve, wherein the flow restriction device is integrated into the actuator.

8. Discharge device according to claim 1, wherein the discharge device comprises a filter for filtering the liquid before flow restriction, said filter being integrated into the flow restriction device as part thereof.

9. Discharge device according to claim 8, wherein the filter is made of molded plastic.

10. Discharge device according to claim 1, wherein the flow rate is 0.01 to 2.0 g/d.

11. Discharge device according to claim 1, wherein the flow rate is adjustable.

12. Discharge device according to claim 1, wherein an average or hydraulic diameter of the capillary channel is between 1 µM and 1 mm.

13. Discharge device according to claim 1, wherein the capillary channel has a length of between 1 mm and 10 m.

14. Discharge device according to claim 1, wherein the capillary channel comprises a portion with a reduced diameter or cross section that results in higher capillary forces in the portion.

15. Discharge device according to claim 1, wherein the capillary channel has a variable effective length or diameter for changing the flow rate.

16. Discharge device according to claim 1, wherein the flow restriction device comprises multiple capillary channels connected in parallel.

17. Discharge device according to claim 16, wherein the capillary channels are variably used for changing the flow rate.

18. Discharge device according to claim 1, wherein the capillary channel is formed by a structured or molded body made of plastic.

19. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the channel is one of a spiral or a meander shape;
further comprising an actuator for actuating the valve, wherein the flow restriction device is integrated into the actuator.

20. Discharge device according to claim 1, wherein the flow restriction device and the evaporator are positioned adjacent to each other.

21. Discharge device according to claim 1, wherein the flow restriction device is integrated into the evaporator.

22. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the channel is one of a spiral or a meander shape;

wherein the evaporator is protected by one of a cap, cover, screen and actuator.

23. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the channel is one of a spiral or a meander shape;
further comprising an actuator for actuating the valve, wherein the evaporator is integrated into the actuator.

24. Discharge device according to claim 1, wherein the evaporator has an evaporator surface so that the liquid forms an essentially uniform film on the evaporator surface.

25. Discharge device according to claim 4 wherein an average or hydraulic diameter of the at least one capillary channel is between 1 μm and 1 mm.

26. Discharge device according to claim 4 wherein the capillary channel has a length of between 1 mm and 10 m.

27. Discharge device according to claim 4, wherein the at least one capillary channel comprises a portion with a reduced diameter or cross section that results in higher capillary forces in the portion.

28. Discharge device according to claim 4, wherein the at least one capillary channel has a variable effective length or diameter for changing the flow rate.

29. Discharge device according to claim 4, wherein the at least one channel comprises multiple capillary channels connected in parallel.

30. Discharge device according to claim 29, wherein the capillary channels are variably used for changing the flow rate.

31. Discharge device according to claim 4, wherein the at least one capillary channel is formed by a structured or molded body made of plastic.

32. Discharge device according to claim 4, wherein the flow restriction device and the evaporator are positioned adjacent to each other.

33. Discharge device according to claim 4, wherein the flow restriction device is integrated into the evaporator.

34. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the liquid is pressurized by one of liquified gas or compressed gas;
wherein the evaporator is protected by one of a cap, cover, screen and actuator.

35. Discharge device according to claim 4, wherein the evaporator has an evaporator surface so that the liquid forms an essentially uniform film on the evaporator surface.

36. Discharge device according to claim 7, wherein the flow restriction device is positioned adjacent to the valve.

37. Discharge device for evaporating a liquid, comprising:
a container for holding a pressurized liquid;
a valve connected to the container for controlling release of the pressurized liquid having an open state and a closed state;
a flow restriction device coupled to the valve; and,
an evaporator coupled to the flow restriction device, wherein the flow restriction device restricts the flow rate of the liquid from the container to the evaporator in the open state of the valve below or substantially equal to a rate of evaporation of the liquid by the evaporator determined by the length and diameter of at least one channel forming the flow restriction device, so that the valve can be in the open state permanently for continuous release and evaporation of the liquid, and wherein the valve can be locked in the open state;
further comprising an actuator for actuating the valve, wherein the evaporator is integrated into the actuator.

38. Discharge device according to claim 7, wherein the evaporator has an evaporator surface so that the liquid forms an essentially uniform film on the evaporator surface.

* * * * *